United States Patent [19]

Sih

[11] 4,312,983

[45] Jan. 26, 1982

[54] 2-DECARBOXY-2-TETRAZOLYL-19-HYDROXY-19-METHYL-6A-CARBA-PGI$_1$ COMPOUNDS

[75] Inventor: John C. Sih, Kalamazoo, Mich.

[73] Assignee: The Upjohn Company, Kalamazoo, Mich.

[21] Appl. No.: 126,497

[22] Filed: Mar. 3, 1980

Related U.S. Application Data

[62] Division of Ser. No. 54,720, Jul. 5, 1979, Pat. No. 4,225,507.

[51] Int. Cl.$^3$ .................... C07D 257/04; A61K 31/41

[52] U.S. Cl. .................... 542/429; 548/253; 424/269

[58] Field of Search .................... 548/253; 542/429

Primary Examiner—Donald G. Daus
Assistant Examiner—D. B. Springer
Attorney, Agent, or Firm—L. Ruth Hattan; Robert A. Armitage

[57] ABSTRACT

The present invention provides novel 2-decarboxy-2-tetrazolyl-19-hydroxy-19-methyl-6a-carba-PGI$_1$ sulfonylamides which are useful for pharmacological purposes, e.g., anti-asthmatic indications.

1 Claim, No Drawings

2-DECARBOXY-2-TETRAZOLYL-19-HYDROXY-19-METHYL-6A-CARBA-PGI₁ COMPOUNDS

DESCRIPTION

CROSS REFERENCE TO RELATED APPLICATION

The present invention is a divisional application of U.S. Ser. No. 054,720, filed July 5, 1979, now U.S. Pat. No. 4,225,507

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-tetrazolyl-19-hydroxy-19-methyl-6a-carba-PGI₂ compounds. The novel prostacylin analogs are useful for pharmacological purposes, e.g., as anti-asthmatic agents. The preparation and use of these compounds is incorporated here by reference from U.S. Pat. No. 4,225,507.

PRIOR ART

For background on prostacyclin, see for example, R. A. Johnson, et al., Prostaglandins 12, 915-928 (1976) and R. A. Johnson, et al., J. Am. Chem. Soc. 100, 7690-7704 (1978), and, as to pharmacological activity, the references cited therein. For analogs of prostacyclin, see, for example, J. Fried, et al., Proc. Natl. Acad. Sci. U.S.A. 74, 2199-2203, K. C. Nicolaou, et al., J.C.S. Chem. Comm. 1977, 331-332, N. A. Nelson, J. Am. Chem. Soc. 99, 7362-7363 (1977), and K. Kojima, et al., Tetra. Letters, 1978, (1977), and K. Kojima, et al., Tetra. Letters, 1978, 3743-3746. Regarding the nomenclature for analogs of PGI₂, see R. A. Johnson, et al., Prostaglandins 15, 737-740 (1978).

SUMMARY OF THE INVENTION

The present invention particularly provides a prostacyclin-type compound of the formula

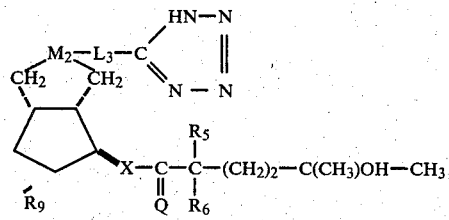

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2$—CH=CH—;
wherein $M_2$ is

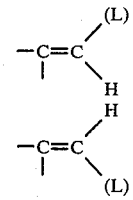

wherein Q is oxo, α-H:β-H, α-OH:β-$R_4$, or α-$R_4$:β-OH, wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;
wherein $R_9$ is hydrogen or hydroxyl; and
wherein X is
(1) trans-CH=CH—,
(2) cis-CH=CH—,
(3) —C≡C—, or
(4) —$CH_2CH_2$—.

I claim:
1. A prostacyclin-type compound of the formula

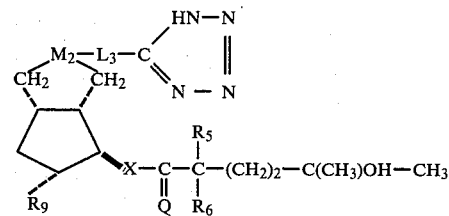

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2$—CH=CH—;
wherein $M_2$ is

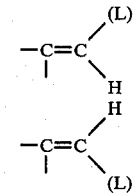

wherein Q is oxo, α-H:β-H, α-OH:β-$R_4$, or α-$R_4$:β-OH, wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;
wherein $R_9$ is hydrogen or hydroxyl; and
wherein X is
(1) trans-CH=CH—,
(2) cis-CH=CH—,
(3) —C≡C—, or
(4) —$CH_2CH_2$—.

* * * * *